United States Patent [19]
Miller et al.

[11] Patent Number: 5,859,191
[45] Date of Patent: Jan. 12, 1999

[54] METHOD FOR THE SITE-SPECIFIC MODIFICATION OF PEPTIDE ALPHA AMINES

[75] Inventors: Stephen Miller; Thomas S. Scanlan, both of San Francisco, Calif.

[73] Assignee: The Regents of the University of California, Oakland, Calif.

[21] Appl. No.: 761,023

[22] Filed: Dec. 5, 1996

[51] Int. Cl.[6] .......................... C07K 1/08; G01N 33/566; G01N 33/543; G01N 33/53
[52] U.S. Cl. .......................... 530/337; 530/333; 530/334; 530/335; 436/501; 436/518; 435/7.1
[58] Field of Search .................................... 530/333, 334, 530/335, 337; 435/7.1; 436/501, 518

[56] References Cited

U.S. PATENT DOCUMENTS

| | | |
|---|---|---|
| 4,108,846 | 8/1978 | Meienhofer . |
| 4,219,497 | 8/1980 | Plattner et al. ..................... 260/501.14 |
| 5,010,175 | 4/1991 | Rutter et al. . |
| 5,182,366 | 1/1993 | Huebner et al. . |
| 5,225,533 | 7/1993 | Rutter et al. . |
| 5,266,684 | 11/1993 | Rutter et al. . |
| 5,420,246 | 5/1995 | Rutter et al. . |
| 5,438,119 | 8/1995 | Rutter et al. . |
| 5,463,564 | 10/1995 | Agrafiotis et al. ..................... 364/496 |
| 5,545,568 | 8/1996 | Ellman . |
| 5,556,762 | 9/1996 | Pinilla et al. . |
| 5,565,324 | 10/1996 | Still et al. . |
| 5,573,905 | 11/1996 | Lerner et al. . |

OTHER PUBLICATIONS

Fukuyama et al. 2,4–dinitrobenzenesulfonamides: A Simple and Practical Method for the Preparation of a Variety of Secondary Amines and Diamines. Tetrahedron Letters, vol. 38(33):5831–5834, 1997.

Handbook of Chemistry and Physics, 61st edition, 1980–1981, CRC Press Boca Raton Florida see pp. D–167, 1981.

Zwierzak, A and Podstawczynska, I., Phase–Transfer Catalyzed Alkylation of Diphenylphosphinic amide—A New Versatile Synthesis of Primary and Secondary Amines. Angew. Chem. Int. Ed. Engl. vol. 16, No. 10. pp. 702–704, 1977.

Advanced Organic Chemistry, Part B: Reactions and synthesis 3ird edition. Francis A. Carey and Richard J. Sundberg. Plenum Press, New York, 1990.

Advanced Organic Chemistry, 4 edition. Jerry March. John Wiley and Sons, New York, 1992.

Ali, F., et al., 1994, "Conformationally constrained peptides and semipeptides derived from RGD as potent inhibitors of the platelet fibrinogen receptor and platelet aggregation," *J. Med. Chem.* 37:769–80.

Blake, J., et al., "Use of combinatorial peptide libraries to construct functional mimics of tumor epitopes recognized by MHC class I–restricted cytolytic T lymphocytes," 1996, *J. Exp. Med.* 184:121–30.

Blondelle, S.E., et al., 1996, "Rapid identification of compounds with enhanced antimicrobial activity by using conformationally defined combinatorial libraries," *Biochem. J.* 313:141–7.

(List continued on next page.)

*Primary Examiner*—Lora M. Green
*Assistant Examiner*—Joseph W. Ricigliano
*Attorney, Agent, or Firm*—Bozicevic & Reed LLP; Pamela J. Sherwood; Bret E. Field

[57] ABSTRACT

A peptide comprising a free terminal alpha amine is treated with an aryl sulfonamide activating agent, resulting in an activated amide. The resulting activated amide is deprotonated with a base and modified by the addition of a substituent group. The aryl sulfonamide activating group is cleaved using a nucleophilic substitution reaction. The method is particularly useful for the modification of peptides at specific N-alpha positions, and is compatible with conventional solid phase peptide synthesis, including those that utilize Fmoc protecting groups.

17 Claims, 2 Drawing Sheets

OTHER PUBLICATIONS

Fukuyama, T., et al., 1995, "2–and 4–nitrobenzenesulfonamides: Exceptionally versatile means for preparation of secondary amines and protection of amines," *Tetrahedron Let.* 36(36):6373–6374.

Han, H., et al., 1995, "Liquid–phase combinatorial synthesis," *Proc. Natl. Acad. Sci. USA* 92(14):6419–23.

Kaljuste, K., and Unden, A., 1993, "New method for the synthesis of N–methyl amino acids containing peptides by reductive methylation of amino groups on the solid phase," *Int. J. Peptide Protein Res.* 42:118–124.

Krchnak, V., et al., 1995, "Linear presentation of variable side–chain spacing in a highly diverse combinatorial library," *Peptide Research* 8(4):198–205.

McBride, J.D., et al., 1996, "Selection of chymotrypsin inhibitors from a conformationally–constrained combinatorial peptide library," *J. Mol. Biol.* 259:819–27.

Merrifield, R.B., 1969, "Solid–phase peptide synthesis," *Advances in Enzymology* 32:221–296.

Ostresh, et al., 1994, "Libraries from libraries: Chemical transformation of combinatorial libraries to extend the range and repertoire of chemical diversity," *Proc. Natl. Acad. Sci. USA* 91:11138–42.

Perez–Paya, E., et al., 1996, "Functionalized protein–like structures from conformationally defined synthetic combinatorial libraries," *J. Biol. Chem.* 271:4120–6.

Rizo, J., and Gierasch, L.M., 1992, "Constrained peptides: Models of bioactive peptides and protein substructures," *Ann. Rev. Biochem.* 61:387–418.

Schmidt, R., et al., 1995, "Structure–activity relationships of dermorphin analogues containing N–substituted amino acids in the 2–position of the peptide sequence," *Int. J. Peptide Protein Res.* 46:47–55.

Schwesinger, R., 1985, "Extremely strong, non–ionic bases: synthesis and applications," *Chimia* 39(9):269–72.

Bowman, Russell W., et al., "A Facile Method for the N–Alkylation of $\alpha$–Amino Esters," *Tetrahedron* (1997) vol. 53, No. (46):15787–15798.

Greene, Theodora W., "Protective groups In Organic Synthesis," *J. Org. Chem.* (1971) vol. 36:282–287.

Miller, Stephen C., et al., "Site–Selective N–Methylation of Peptides on Solid Support," *J. Am. Chem. Soc.* (1997) vol. 119:2301–2302.

METHOD FOR THE SITE-SPECIFIC MODIFICATION OF PEPTIDE ALPHA AMINES

Site-specific modifications of polymers such as polypeptides, having primary amines, requires a chemoselective deprotonation of the reactive nitrogen. Such reactions have been difficult to achieve, because of the selectivity that is required. Such reactions are of interest, however, because they allow manipulation of the properties of pharmaceutically interesting compounds such as proteins, peptides and peptidomimetics.

N-methyl amino acid substitutions have often been used to increase the potency or selectivity of a peptide ligand. This type of modification largely restricts the flanking amino acid sequences in a peptide to the extended region of conformational space (Manlavan and Momany). However, several practical problems are associated with the use of N-methyl amino acids, which have limited their widespread use. Many N-methylated amino acids are not commercially available as protected derivatives suitable for solid-phase peptide synthesis. The purity of commercially available N-methyl amino acids can also cause problems.

Solid-phase peptide synthesis (SPPS) is the method of choice for preparing synthetic polypeptides, because of the speed and convenience of operation. In general, each additional monomer in the chain has its amino group protected. Commonly used protecting groups are tert-butyloxycarbonyl (Boc), and base labile 9-fluorenylmethyloxycarbonyl (Fmoc). The wide-spread use of SPPS, makes it highly desirable that reactions to modify peptides and similar polymers are compatible with Fmoc and Boc chemistry.

Innovations in peptide chemistry have allowed the synthesis of combinatorial libraries consisting of large numbers of peptides and peptide derivatives. These libraries are then usable in numerous in vitro and in vivo screening assays. The successful use of such libraries has been reported for such uses as antimicrobial agents, antigens, enzyme inhibitors, etc. The number of possible molecules that can be made in such libraries would be greatly expanded by the development of SPPS compatible reactions for site-specific N modification.

Relevant Literature

The effect of conformational restriction, such as N-methylation, on the biological activity of a peptide is discussed in Rizo (1992) *Ann. Rev. Biochem.* 61:387–418. Structure-activity relationships of dermorphin analogs containing N-substituted amino acids are described in Schmidt et al (1995) *Int. J. Peptide Protein Res.* 46:47–55. Conformationally constrained peptides and semipeptides derived from RGD are described in Ali et al. (1994) *J. Med. Chem.* 37:769–780.

Synthesis of N-methyl amino acid-containing peptides on solid phase, using formaldehyde, is described by Kaljuste and Unden (1993) *Int. J. Peptide Protein Res.* 42:118–124. Some of the drawbacks of the method are its limitation to Boc protecting groups, poor methylation of many side chains, side reactions, and probable racemization of the peptide. Methods for the solid-phase synthesis of peptides may be found in Merrifield (1969) Advances in Enzymology 32:221–295, and in Meienhofer, U.S. Pat. No. 4,108,846.

The very strong, non-ionic base MTBD, 7-methyl-1,5,7-triazobicyclo [4.4.0]dec-5-ene is described by Schwesinger (1985) *Chimia* 39:269–271. The use of 2- and 4-nitrobenzenesulfonamides for activation and alkylation of amines is described in Fukuyama et al. (1995) *Tetrahedron Lett* 36:6373–6374.

Screening of peptide combinatorial libraries is discussed in Blake et al. (1996) *J. Exp. Med.* 184:121–130; McBride et al (1996) *J. Mol. Biol.* 259:819–827; Blondelle et al. (1996) Biochem. J. 313:141–147, among others.

The modification of combinatorial libraries by permethylation is described by Ostresh et al. (1994) *P.N.A.S.* 91:11138–11142. Methods of creating combinatorial libraries are discussed in Perez-Paya et al. (1996) *J. Biol. Chem.* 271:41204126; Krchnak et aL (1995) *Pept. Res.* 8:198–205; and Han et al. (1995) *P.N.A.S.* 92:6419–6423. U.S. Patents disclosing methods of creating combinatorial libraries include U.S. Pat. Nos. 5,573,905 (Lerner et al.); 5,565,324 (Still et al.); 5,556,762 (Pinilla et al.);5,545,568 (Ellman); 5,010,175 (Rutter); 5,266,684 (Rutter); 5,225,533 (Rutter); 5,438,119 (Rutter); 5,420,246 (Rutter) and 5,182,366 (Huebner).

SUMMARY OF THE INVENTION

A method is provided for site-selective reactions of primary amines, where one of the amino group hydrogens is replaced with a substituent group. Reactions of interest involve compounds, polymers, or mixtures and libraries thereof, in which there are groups or atoms that could be susceptible to the reactions that modify the target primary amino group, for example a polyamide or library of polyamides. More particularly, polypeptides and polypeptide analogs are modified at the N-alpha position by the subject methods during solid-phase peptide synthesis to introduce substituent groups, e.g. alkyl, aryl or allyl groups, at specific residues.

A compound having a free amine is treated with an activating agent that reacts with the nitrogen of the amine to create a reactive amide. The resulting amide is selectively deprotonated with a strong base, and then modified by the addition of a substituent group. In the last step, the activating group is cleaved by a mild chemical treatment that does not affect other functional groups in the molecule. The method is compatible with conventional solid-phase peptide synthesis methods, including those that utilize Fmoc protecting groups. The procedure does not cause detectable racemization of polypeptides.

BRIEF DESCRIPTION OF THE DRAWINGS

FIG. 2a depicts the spectrum for (N—Me)SFLLRN—$NH_2$. FIG. 2b depicts the spectrum for S(N—Me)FLLRN—$NH_2$.

DESCRIPTION OF THE SPECIFIC EMBODIMENTS

Figure 1:
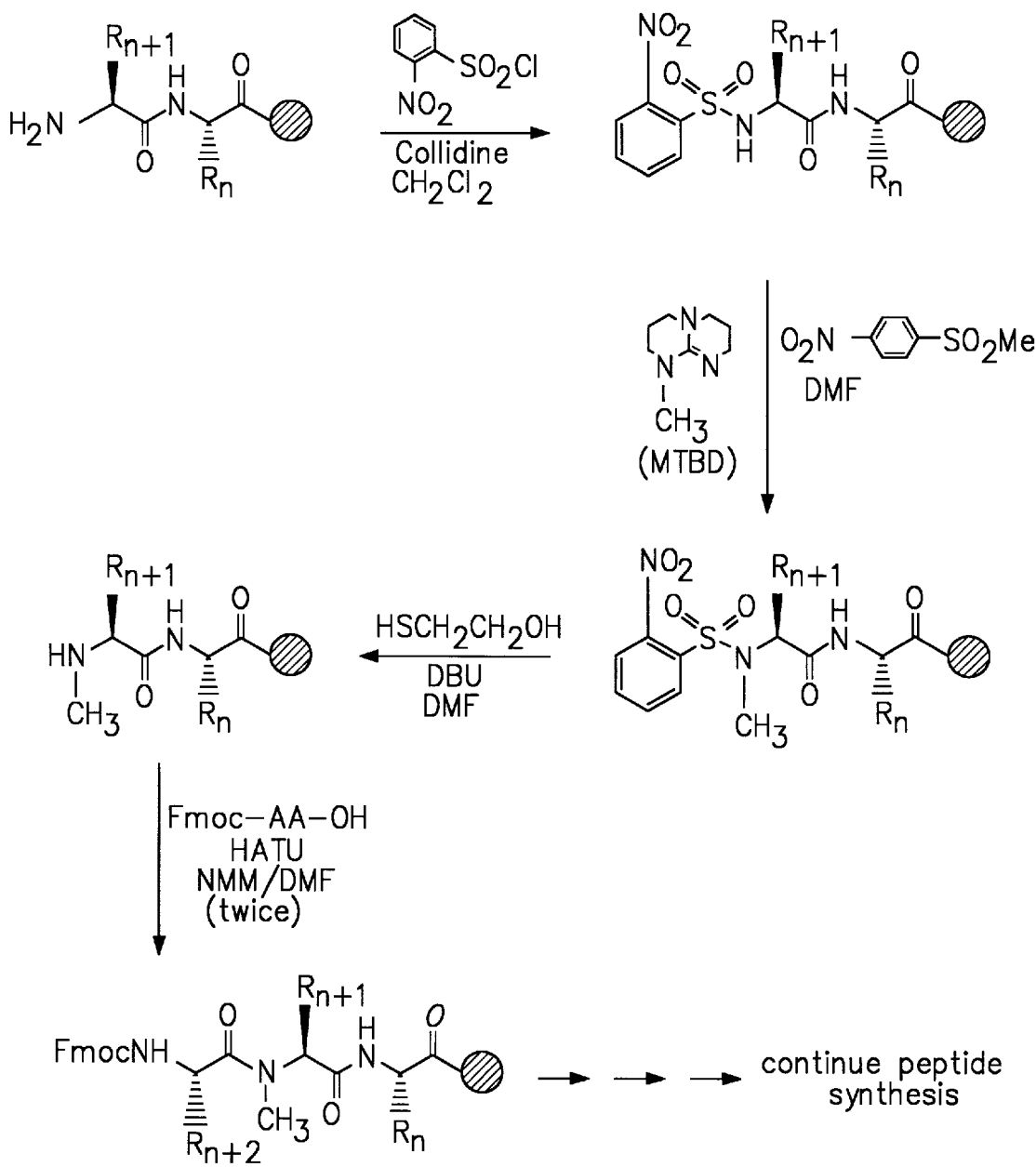
FIG. 1 illustrates an exemplary reaction scheme for selective N-methylation of peptides.

A method is provided for site-selective addition reactions of primary amines that are present on compounds, polymers, or mixtures and libraries thereof, in which there are groups or atoms that could be susceptible to the reactions that modify the target primary amino group. A compound, e.g. a polymer such as a polyamide, having a free amine is treated with an activating agent that reacts with the nitrogen of the amine to create a reactive amide. The resulting amide is selectively deprotonated with a strong base, and then modified by the addition of a substituent group. The activating group is then cleaved off to leave the substituted, secondary amine.

The method is compatible with conventional solid-phase peptide synthesis, including those that utilize Fmoc protecting groups. The procedure does not cause detectable racemization of polypeptides. The method provides a powerful tool for site-specific N-modification of polymers, particularly peptides and peptide analogs synthesized on a solid support, using commercially available chemicals. This method can easily be automated, and provides a general procedure for N-alpha-modification of bioactive peptides. The method can be used in a number of combinatorial strategies, for producing large libraries of N-modified peptides and other amines.

Before the present solid phase synthesis methodology is disclosed and described, it is to be understood that the method of this invention is not limited to the particular monomer or oligomer that can be prepared. The conditions and techniques described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", and "the" include plural referents unless the context clearly dictates otherwise. Thus, for example, reference to "a reactant" includes a plurality and/or mixture of such reactants, reference to "the polymer" includes a plurality and mixture of said polymers and so forth.

Abbreviations

Chemical abbreviations used herein are as follows:
9-fluorenylmethyloxycarbonyl (Fmoc); tert-butyloxycarbonyl (Boc); solid-phase peptide synthesis (SPPS); 7-methyl-1,5,7-triazobicyclo[4.4.0]dec-5-ene (MTBD); methyl p-nitrobenzene sulfonate (methyl nosylate); 1,8-diazobicyclo[5.4.0]undec-7-ene (DBU); dimethylformamide (DMF); dimethylacetamide (DMA); o- and p-nitrobenzenesulfonyl (oNBS and pNBS); trifluoroacetic acid (TFA); o(7-azabenzotriazol-1-yl-n,n,n',n'-tetramethyluronium hexafluoro phosphate (HATU); polypeptide nucleic acids (PNA); hydroxybenzotriazole tetramethyl uronium hexafluoro phosphate (HBTU); benzotriazole-1-yl-oxy-tris (dimethylamino) phosphonium hexafluorophosphate (BOP); N-methyl morpholine (NMM); 4-methyl benzhydrylamine (MBHA); pentamethylguanidine (PMG); tetramethylguanidine (TMG); 1,5-diazabicyclo[4.3.0]non-5-ene (DBN); tetrabutyl ammonium fluoride (TBAF).

Definitions

The following definitions are used in describing the subject invention:

Solid support. A substrate or solid support is a conventional solid support material used in peptide synthesis, including polymeric and spherical beads. Non-limiting examples of such substrates or supports include a variety of support resins and connectors to the support resins such as those that are photo-cleavable, DKP-forming linkers (DKP is diketopiperazine; see WO90/09395, herein incorporated by reference), TFA cleavable, HF cleavable, fluoride ion cleavable, reductively cleavable; Pd(O) cleavable; nucleophilically cleavable; radically cleavable; and base-labile linkers.

Substrate compound: A compound containing at least one primary amine that is modified by the subject methods, and in which there are groups or atoms that could be susceptible to the reactions that modify the target primary amino group. Compounds of interest include various monomers and polymers, particularly polymers. Polymers include addition polymers and condensation polymers, more particularly polyamides. Polyamides of interest include polypeptides, which as used herein include analogs and mimetics where the amino acid monomers in the polypeptide may have naturally occurring or modified side chains, which may also include polypeptide nucleic acids, or combinations thereof. See, for example, PCT publication US93/09117 (Zuckerman) and US91/04292 (Bartlett). The subject methods find particular use in polypeptides, where modification of specific residues is of interest.

Protecting group. Any group that is capable of preventing the atom to which it is attached, usually oxygen or nitrogen, from participating in an undesired reaction or bonding, usually in a synthesis reaction. Protecting groups are also known to prevent reaction or bonding of carboxylic acids, thiols and the like. Such groups and their preparation and introduction are conventional in the art, and include salts, esters and the like. Protecting groups commonly used in solid phase peptide synthesis include Fmoc and Boc groups, which protect the primary amine of incoming amino acid monomers during formation of the peptide bond. Protecting groups are commonly used to protect amino acid side chains during peptide synthesis, for example TFA-labile tBu, Trt, Pmc and Boc; Pd(O)-labile Alloc, OAII; photolabile groups such as nitro veritryl oxycarbonyl (NVOC); and fluoride labile groups such as trimethylsilyl oxycarbonyl (TEOC).

Activating group: any group that, on reaction of the target primary amine in the substrate compound with an activating agent, renders an amide nitrogen that is more reactive than any other nitrogen in the substrate compound. The activating group renders the target NH group more acidic than other nitrogens in the substrate compound. For the purposes of the subject invention, the activating group is preferable cleavable from the amide under conditions that are compatible with conventional amino acid protecting groups and a polyamide backbone. Exemplary activating agents react with the primary amine to form a sulfonamide, although other structures, such as trifluoroacetamide, may also be formed. Table I provides an overview of some exemplary sulfonamide activating groups, and methods by which they are cleaved from the substrate compound.

Various sulfonyl halides have been used as activating compounds. The working examples demonstrate the utility of aryl sulfonyl halides, where the aryl moiety is substituted with an electron withdrawing group, e.g. a nitro substituent, at the ortho or para position. For alkylation reactions of polypeptides, ortho-nitrobenzenesulfonyl chloride and para-nitrobenzenesulfonyl chloride are exemplary activating agents, yielding oNBS and pNBS amides, respectively.

TABLE 1

| Cleavage Mechanism | Activating Group |
|---|---|
| Base Labile | 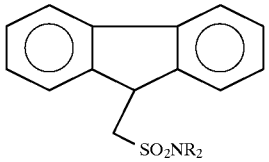 |

TABLE 1-continued

| Cleavage Mechanism | Activating Group |
|---|---|
| Base Labile | $O_2N$-C$_6$H$_4$-CH$_2$CH$_2$-SO$_2$NR$_2$ |
| Base Labile | electron withdrawing group-CH(H)-CH$_2$-SO$_2$NR |
| F$^-$ Labile | Me$_3$Si-CH$_2$CH$_2$-SO$_2$NR |
| F$^-$ Labile | R-C$_6$H$_4$-CH(CH$_2$SiMe$_3$)-CH$_2$-SO$_2$NR |
| F$^-$ Labile | Me$_3$Si-CH(C$_6$H$_4$-R)-CH$_2$-SO$_2$NR |
| PD(0) labile | CH$_2$=CH-CH$_2$-SO$_2$NR$_2$ |
| Photolabile | (MeO)$_2$C$_6$H$_2$(NO$_2$)-CH(CH$_3$)-SO$_2$NR$_2$ |
| Radical Cleavage | pyridyl-N-SO$_2$NR$_2$ |
| Nucleophilic Aromatic Substitution | C$_6$H$_4$(Electron withdrawing group)-SO$_2$NR$_2$ |
| Nucleophilic Aromatic Substitution | (Electron withdrawing group)-C$_6$H$_4$-SO$_2$NR$_2$ |
| Nucleophilic Aromatic Substitution | (Electron withdrawing group)$_2$-C$_6$H$_3$-SO$_2$NR$_2$ |
| Nucleophilic Aromatic Substitution | (Electron withdrawing group)$_3$-C$_6$H$_2$-SO$_2$NR$_2$ |
| Nucleophilic Aromatic Substitution | pyrimidinyl-SO$_2$NR$_2$ |
| Nucleophilic Aromatic Substitution | pyridyl(N at 3)-SO$_2$NR$_2$ |
| Nucleophilic Aromatic Substitution | pyridyl(N at 4)-SO$_2$NR$_2$ |
| Nucleophilic Aromatic Substitution | pyridyl(N at 2)-SO$_2$NR$_2$ |
| Nucleophilic Aromatic Substitution | (Electron Withdrawing Group)-pyridyl-SO$_2$NR$_2$ |
| Nucleophilic Aromatic Substitution | (Electron Withdrawing Group)-pyridyl-SO$_2$NR$_2$ |

Strong base: strong bases useful in the subject methods are capable of selective deprotonation of the activated amide. Hindered guandidinium bases are exemplary, where there is sufficient substitution so as not to act as a nucleophile in the reaction. The pKa of the base will be in the range of about 12 to 15. For ease of use and stability considerations, non-ionic bases are preferred. Examples include MTBD, DBU, DBN, PMG, TMG, low equivalents of BEMP, the ionic base TBAF, TBD and derivatives, and the like.

Modifying agent: an electrophilic agent that will selectively modify the deprotonated, activated amide to add a substituent group. Preferred modifying agents are not strong enough to modify the amide backbone of a polypeptide. Exemplary are alkylating agents such as alkyl nosylates, e.g. methyl nosylate; alkyl halides, e.g. ethyl iodide; allyl bromide; benzyl bromide, propyl iodide; alkyl sulfates, e.g. dimethyl sulfate; Pd-π allyl species; Mitsunobu reactions (Mitsunobu (1981) Synthesis:1), particularly for intramolecular, e.g. cyclization, reactions; and other agents as known in the art.

Substituent, substituted or derivative substituent describes an atom or radical which is part of a first molecule in that it replaces another atom or radical of the first molecule. When a molecule is substituted, it is a derivative of a molecule bearing one or more substituent. Useful substituents in any of the peptides of the invention include halo, alkyl, alkoxy, aryl, allyl, alkylthio, haloalkyl, haloalkoxy, halothio, and the like, which replace a hydrogen attached to a primary amine.

Alkyl substituents: a hydrocarbon or substituted hydrocarbon group. Alkyls may be linear or branched. Substituted alkyls may have hetero groups, including nitro-, oxy-, hydroxy-, thio-, carbonyl-, halo-, amino, and the like, as known in the art. Preferably, substituent groups are not located on the alpha carbon of the alkyl group.

Aryl substituents: a benzyl or substituted benzyl group. Substituted aryls may have hetero groups, as described for alkyl substituents. These types of modifications may be carried out using reductive alkylation, as known in the art.

Allyl substituents: a hydrocarbon having one or more unsaturated C—C bonds. Allyls may be linear or branched. Substituted allyls having hetero groups as described for alkyl substituents may also be used. Alkynes, particularly terminal alkynes may be used. Alkyne substituents may be modified in a second reaction by various known methods, including Sonogashira reactions, hydrozirconation, etc.

Cleavage agent: a compound capable of cleaving the substituted target amide to release the activating group. Some reagents of interest are listed in Table 1, including Pd(O), fluoride ion, radical cleavage, bases, photolysis, and nucleophilic aromatic substitution. Cleavage agents of interest for use with nucleophilic aromatic substitution include alkyl and aryl thiols, such as β-mercaptoethanol and thiophenol, dithiothreitol, glutathione, n-propylthiol, ethanedithiol, n-butylthiol, etc. Other reagents include hydrazine, pyrrolidine, piperidine, etc.

Coupling agent: agents, as known in the art, that activate coupling reactions in polypeptide synthesis. It is known that secondary amines, such as those formed by the subject methods, are more difficult to couple than primary amines. While use of HBTU or BOP as a coupling agent is conventional for SPPS, it may be necessary to use a stronger agent, for example HATU, to achieve a high yield in the synthesis step involving the secondary amine, and/or to drive the coupling reaction to completion by using multiple cycles of coupling reactions.

Solvents: suitable inert solvents include blocked amides, such as dimethylformamide, sulfoxides, such as dimethylsulfoxide ;dimethyl acetamide; methylene chloride; and the like.

Side chains: the substituent groups of naturally occurring amino acids, or analogs and modified versions thereof. Side chains include —$CH_3$ of alanine; —$CH(CH_3)_2$ of valine; —$CH_2CH(CH_3)_2$ of leucine; —$CH(CH_3)CH_2CH_3$ of isoleucine; —$CH_2OH$ of serine; —$CHOHCH_3$ of threonine; —$CH_2SH$ of cysteine; —$CH_2CH_2SCH_3$ of methionine; —$CH_2$-(phenyl) of phenylalanine; —$CH_2$-(phenyl)-OH of tyrosine; —$CH_2$-(indole) of tryptophan; —$CH_2COO$— of aspartic acid; $CH_2C(O)(NH_2)$ of asparagine; $CH_2CH_2COO$—of glutamic acid; —$CH_2CH_2C(O)NH_2$ of glutamine; —$CH_2CH_2CH_2$—N—(H)—$C(NH_2)^+NH_2$ of arginine; —CH2-(imidazole)+group of histidine; and —$CH_{2^1}(CH_2)_3NH_3^+$of lysine.

Library: library and mixture are used herein to describe three or more substrate compounds together, where each of the substrate compounds comprise at least one primary amine. Preferably the mixture includes 10 or more, 100 or more, 1,000 or more, 10,000 or more, 100,000 or more or 1,000,000 or more distinct and different compounds, e.g. different polypeptides with different amino acid sequences.

Reaction Steps

Each step of the reaction is usually conducted at about ambient temperature of 20° C. and pressure of one atmosphere. However, the reaction can also be carried out over a wide range of temperatures of about −78° C. to about 150° C., and varies depending on the solvent used. Depending on the temperature, the time of the reaction can vary between about 5 minutes to about 24 hours.

Site-selective addition reactions of substrate compounds having primary amines are achieved by the subject methods, using substrate compounds as described above. For brevity, the reactions will be primarily described in terms of modifications of polypeptides. It should be understood, however, that the subject methods are not limited to such uses. The reaction steps may be performed in solution, or with the substrate compound coupled to a solid support resin. In general, solid phase reactions are preferred for their convenience, but the use of a support is not necessary for the reaction chemistry.

The N-alpha modification of polypeptides is most conveniently combined with conventional SPPS, where amino acids are added in a step-wise manner while the chain is anchored on a solid phase resin. A benefit of the subject invention is the compatibility with Fmoc and Boc chemistry, allowing commonly available methods and reagents to be used. The modification reaction is performed at the point in the synthesis when the desired target residue has been added to the nascent chain and has been deprotected, leaving a free primary amine. After the nitrogen has been modified, the peptide synthesis is resumed. In order to achieve high yields, the coupling reaction to the modified, secondary, amine may be repeated, and/or performed with a strong coupling agent.

The substrate compound is treated with an activating agent that reacts with the nitrogen of the amine to create a reactive amide. For reactions involving polypeptides, aryl sulfonyl halides are found to be useful, including o- and p-nitrobenzene sulfonyl chloride. The polypeptide is treated with an excess of activating agent, usually from about 1 to 5 molar equivalents. The choice of solvent is not critical, for example, methylene chloride, toluene, etc. may be used. The reaction is allowed to go to completion, usually from about 10 minutes to 24 hours, more usually from about 0.5 to 2 hours when performed at room temperature.

The resulting amide is selectively deprotonated by addition of a molar excess of strong base, conveniently a non-ionic base, in combination with a modifying agent. Any convenient solvent that is compatible with the base and modifying agent may be used, for example DMA, DMF, etc.

A number of modifying agents can be used at this point in the reaction. Examples include alkylating agents such as methyl nosylate, ethyl iodide, dimethyl sulfate, etc. Allyl groups may be introduced through the use of allyl carbonates, cinnamyl carbonates, vinyl epoxides, e.g. butadiene monoxide and analogs, etc. activated with palladium (0), where the allyls may be substituted with various hetero groups of interest.

After washing, the modified polypeptide is treated to cleave the activating group. Typically a large excess of the reagent is added, at least about 2–3 molar excess, and may be as much as a ten-fold molar excess. For nucleophilic aromatic substitutions, any nucleophile that has electronic pro used, i.e. soft nucleophiles. Thiophenol and 2-mercaptoethanol have been used successfully with DMF as a solvent.

On completion of the modification step, polypeptide synthesis may be resumed. As previously noted, double coupling may be desirable.

A number of schemes for generating combinatorial libraries have been described in the scientific and patent literature. U.S. patents include U.S. Pat. Nos. 5,573,905 (Lerner et aL); 5,565,324 (Still et al.); 5,556,762 (Pinilla et al.); and 5,545,568 (Ellman), herein incorporated by reference. The modification methods of the subject invention can readily be included in such prior art combinatorial syntheses, because of the compatibility with conventional solid phase synthesis reactions.

Utility

The individual modified compounds and peptides of the invention are useful in a variety of ways similar to that of unsubstituted peptides and oligomers. For example, they can have one or more properties in binding to various moieties, including proteins, such as enzymes, receptors, antibodies and the like, nucleic acids, carbohydrates, lipids, they can react with enzymes to form products or have other properties such as antigenic compounds for vaccines or diagnostic reagents, including as probes. Compounds can also be used as enzyme inhibitors and in connection with affinity chromatography.

The chemical synthesis methodology of the present invention has utility with respect to producing a wide range of modified compounds and in particular modified peptides. The invention is particularly useful with respect to the modification of a mixture or library of compounds. For example, the synthesis methodology can be simultaneously applied to a library of peptides in a manner so as to modify different peptides in the library and thereby greatly increase the number of different compounds and the diversity of compounds contained with in the library. The resulting library is then useful in carrying out assay methodology whereby the modified library is screened against another library compound or receptor.

As an example of the utility of the claimed invention, it is possible to create a mixture of peptides containing thousands, tens of thousands, millions and even tens of millions of different peptides. Within the peptide library one can include a large number of different amino acid sequences which sequences correspond to variants of a naturally occurring peptide, protein or portion thereof which bind to a naturally occurring receptor. The library of peptides is then modified using the methodology of the present invention. After modification the library is screened against the same receptor. A series of screening tests can be carried out where the conditions such as concentration or binding affinity are changed so as to find compounds which are particularly selective for and/or bind to the receptor with a relatively high degree of affinity as compared to the naturally occurring peptide or protein. In view of such, the invention includes libraries of compounds which compounds are produced by first providing a diverse library of compounds (e.g., peptides) and then subjecting those compounds to the site specific modification methodology of the present invention. Preferably, the library will include at least one biologically active compound.

EXPERIMENTAL

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade; and pressure is at or near atmospheric.

EXAMPLE 1

N-Methylation of Peptides

N-alkylation was initially attempted via a three-step procedure involving trifluoroacetylation, selective alkylation via the Mitsunobu reaction (as described in Mitsunobu (1981) *Synthesis* 1; Hughes (1992) *Org. Reactions* 42:335–656), and deprotection to afford the N-alkyl amine. No reaction was achieved using Mitsunobu conditions on solid support, nor from "enhanced" Mitsunobu conditions (described in Tsunoda et aL (1995) *Tetrahedron Lett.* 36:2529–2530). N-tosyl and N-mesyl peptides also failed to alkylate under these conditions.

The treatment of N-tosyl-LLONSF on Tentagel resin with alkylating agents and base was subsequently investigated. Methylation of the sulfonamide in DMF with dimethyl sulfate in the presence of the hindered, non-ionic guanidium base MTBD, was selective and complete in less than two hours. The use of MTBD as base was important for achieving high yields, as weaker bases gave poor or no yield of product, and stronger bases were not selective.

Attempts to alkylate N-trifluoroacetyl-LLONSF using 10 eq $Me_2SO_4$ and MTBD gave only 50% product after 24 h. This result prompted exploration for a sulfonamide activating group that could be selectively removed after alkylation. The cleavable alkyl sulfonyl chlorides that were synthesized formed sulfonamides with amines in solution, but failed to yield the sulfonamide when added to the resin bound peptide free amine in methylene chloride.

The failure of alkyl sulfonyl chlorides to couple to the resin led to the use of aryl sulfonyl chlorides, which cannot form sulfones. Initially the deprotection of aryl sulfonamides using photochemical or free-radical mechanisms was contemplated. Instead, the methods described by Fukuyama et al. (1995) *Tetrahedron Lett.* 36:6373–6374 were used to cleave nitrobenzenesulfonamides via nucleophilic aromatic substitution with thiophenol.

Both o- and p-nitrobenzenesulfonyl (oNBS and pNBS) peptides were readily methylated using the conditions described above, but the peptidyl 2,4-dinitrobenzenesulfonamide was not fully methylated even after 48 h. The Mitsunobu reaction failed with all three sulfonamides. Attempted cleavage of oNBS and pNBS with hydrazine and piperidine failed, but was effected with thiophenol and DBU in DMF. The ONBS group cleaved more readily than PNBS, and was used for all subsequent reactions. β-mercaptoethanol was substituted for thiophenol, as it cleaved the sulfonamides faster and is less toxic, less noxious, and more commonly found. Finally, methyl nosylate, a commercially available crystalline solid, was substituted for dimethyl sulfate on the basis of handling and toxicity considerations.

The procedure employs the protection of the resin-bound peptide free amine as the o-nitrobenzenesulfonamide by treatment with the corresponding sulfonyl chloride in $CH_2Cl_2$ containing collidine for two hours. The sulfonamide is then selectively deprotonated with strong, non-ionic base MTBD and alkylated with methyl nosylate in DMF for 30 minutes. Finally, the oNBS group is removed quantitatively with β-mercaptoethanol and DBU in DMF for 30 minutes. The deprotection is easily followed via the formation of a bright yellow color, presumably due to the release of o-nitrobenzenethioethanol. This three step procedure did not cause any detectable racemization.

The N-methyl scanning of SFLLRN-NH2 was performed on 0.1 mmol scale using Rink Amide MBHA resin. The yields are shown in Table II. Standard Fmoc solid-phase peptide synthesis was carried out to the position where N-methylation was desired, the Fmoc group was then removed and the resin bound peptide was treated as shown in FIG. 1. The next amino acid residue was introduced using double coupling with HATU (see Carpino et al. (1993) *J. Am. Chem. Soc.* 115:4397–4398), and standard Fmoc SPPS was continued.

TABLE II

Crude and Purified Peptide Amide Yields

| Peptide Amide | Crude yield[a] | Purified Yield[b] |
|---|---|---|
| (N—Me)SFLLRN | 102.4 mg (85.5%) | 66.5% of theory |
| S(N—Me)FLLRN | 79.5 mg (63.6%) | 32.7%[c] |
| SF(N—Me)LLRN | 95.4 mg (83.7%) | 64.6% |
| SFL(N—Me)LRN | 93.8 mg (88.7%) | 58.7% |
| SFLL(N—Me)RN | 102.8 mg (88.7%) | 63.7% |
| SFLLR(N—Me)N | 84 mg (89.1%) | 48.0% |

[a] crude purity in parentheses assessed by RP-HPLC at 215 nm (10–50% CH3CN in H$_2$O containing 0.1% TFA).
[b] Purified by preparative RP-HPLC (same solvent system) to >99% by HPLC (215 nm). Yield based on manufacturer's stated resin substitution.
[c] Only 91% pure. The lower yield of the (N—Me)Phe peptide was primarily due to poor coupling of the final serine residue. Purification was difficult due to a closely-eluting impurity arising from this coupling step.

The introduction of the oNBS group was quantitative, and the methylation was >95% complete in all cases, however some side-product was formed in the arginine-containing peptide fragments from modification of the Arg(Pmc) residue. This posed no problem for the N-methyl scanning of SFLLRN, as the small amount of side product is easily separated by reverse-phase HPLC. Its formation could also be eliminated entirely by the substitution of arginine with an orthogonally-protected ornithine, which can be guanylated at the completion of the synthesis. Removal of the oNBS group by treatment with β-mercaptoethanol and DBU in DMF proceeded rapidly and quantitatively. The most difficult aspect of the synthesis was the expected difficulty in subsequent coupling of the N-methyl peptides.

Figure 2A:
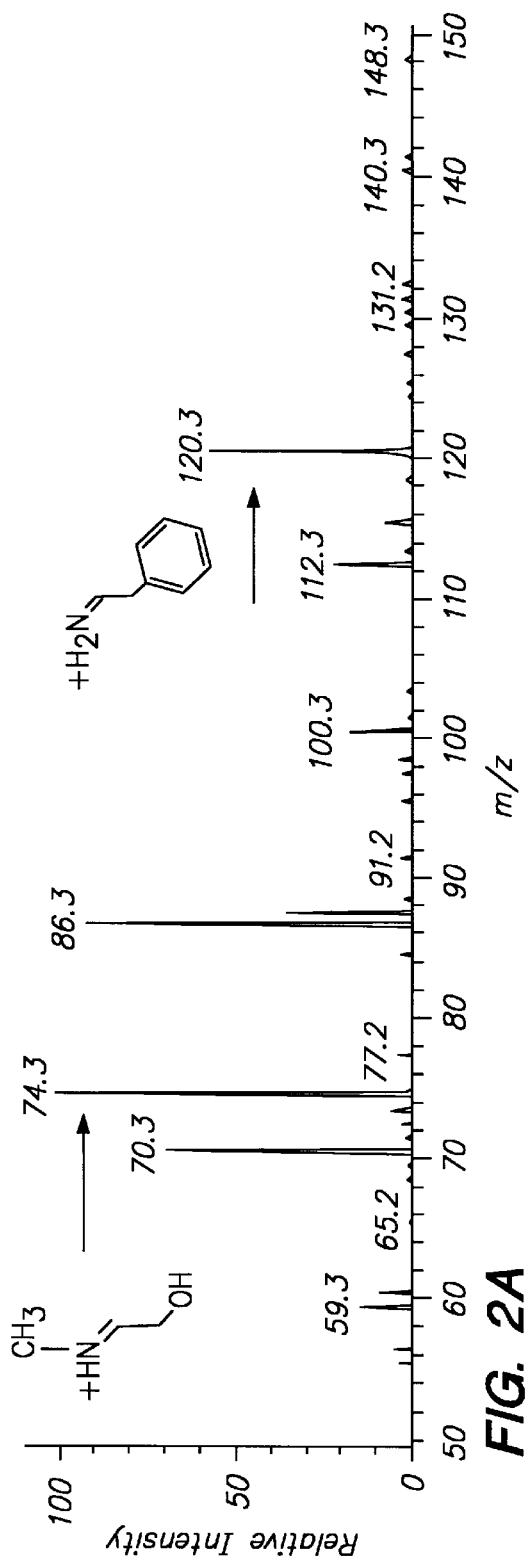
FIGS. 2a and 2b are graphs of immonium ion region of tandem mass spectra.
Figure 2B:
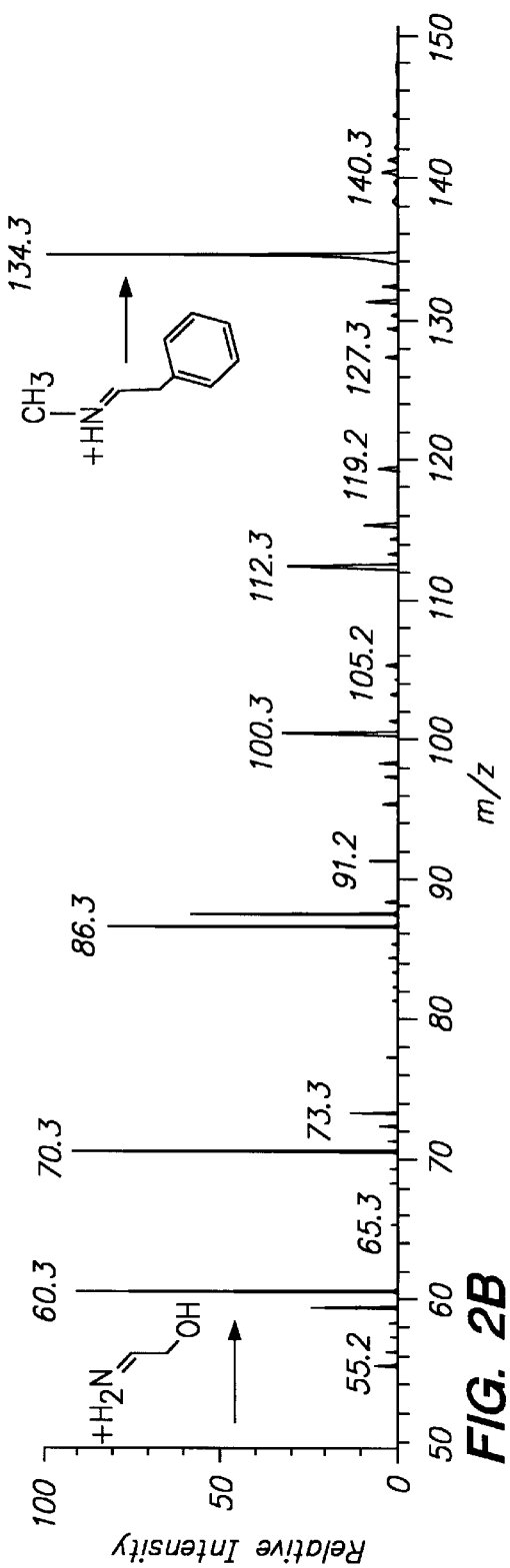

The six N-methylated peptides synthesized have identical masses, differing only in the location of the N-methyl group. However, high energy collision-induced dissociation (CID) analysis with tandem mass spectrometer and matrix-assisted laser desorption ionization post-source decay (MALDI-PSD) mass spectometry both allowed unequivocal assignment of the site of methylation in each peptide. The N-methylated residue is readily identified by its often prominent N-methyl immonium ion peak (data shown in FIGS. 2*a* and 2*b*). Analysis of the peptide fragments was used to corroborate the assignment and to confirm its location in the peptide sequence.

Detailed Materials and Methods

Fmoc-amino acids and HBTU were purchased from Advanced Chemtech. Rink Amide MBHA resin was purchased from Novabiochem. Collidine, 2-nitrobenzenesulfonyl chloride, methyl 4-nitrobenzenesulfonate, 1,3,4,6,7,8-hexahydro-1-methyl-2H-pyrimido [1,2a]pyrimidine, piperidine, ethanedithiol, thioanisole, TFA and HATU were purchased from Aldrich. DMF and NMM were purchased from Fisher. Β-mercaptoethanol was purchased from Sigma.

Peptide synthesis was conducted on a Protein Technologies PS3 peptide synthesizer on 0.1 mmol scale using standard Fmoc SPPS. The following side chain protected amino acids were used: Arg(Pmc), Asn(Trt), Orn(Boc), Ser(OtBu). Each amino acid was coupled sequentially to the Rink Amide MBHA resin (0.55 mmol/g substitution) in four-fold excess using 3.8 equivalents of HBTU in 0.4M NMM/DMF for 20 minutes. Fmoc deprotection was accomplished with 20% piperidine in DMF (2×5 min). When the desired site of methylation was reached, the Fmoc-deprotected peptide resin was removed from the synthesizer, washed with CH$_2$Cl$_2$ and treated with five equivalents of collidine and three equivalents of 2-nitrobenzenesulfonyl chloride in CH$_2$Cl$_2$ for 2 h at room temp. The resin was then washed with and resuspended in DMF and treated with 2–4 equivalents of MTBD followed by 3–5 equivalents of methyl 4-nitrobenzenesulfonate for 30 min at room temp. After washing, the resin was again suspended in DMF and treated with 5 eq DBU and 10 eq 2-mercaptoethanol for 30 min at room temp. A bright yellow solution was indicative of oNBS cleavage. Following cleavage, the resin was extensively washed with DMF, and returned to the synthesizer. The next amino acid in the peptide sequence was double coupled to the resin using HATU in place of HBTU (2×20 min couplings). The remaining amino acids in the peptide were coupled with HBTU, as described. At each step in the N-methylation sequence, a small sample of the resin was removed and cleaved for HPLC and MALDI analysis.

The peptides were cleaved from the resin using a cocktail consisting of 90% TFA, 5% H$_2$O, 2.5% ethanedithiol, and 2.5% thioanisole for 90 minutes, followed by filtering and washing of the resin with TFA. The volume of the TFA solution was reduced by rotary evaporation, and the crude peptide precipitated with ethyl ether. The crude peptide was sedimented and the ether discarded. This was repeated 2–3 times. The crude was dried in vacuo.

The crude peptide was dissolved in 0.1% aqueous TFA and purified on a Dynamax C$_{18}$ preparative HPLC column using a linear gradient of 10–50% acetonitrile in water containing 0.1% TFA. Fractions containing only the desired peptide were pooled and lyophilized, yielding 32–66 mg of purified peptide, >99% pure in all cases except for S(N—Me)FLLRN, which was approximately 91 % pure.

Peptide structures were verified using collision induced dissociation (CID) tandem mass spectrometry. The LSIMS molecular ion peak for all six peptides was 762.4. Immonium ion peaks for all amino acids in each peptide were present, and the site of N-methylation evident from the +14 increase in mass. MALDI-PSD fragmentation occurred at the peptide bond, making sequence analysis straightforward.

The above results demonstrate a powerful new tool for site-specific N-methylation of peptides on solid support using commercially available chemicals. This method can easily be automated, and provides a general procedure for N-methyl scanning of bioactive peptides. It also opens the doors to other modifications of the amide backbone, such as N-allylation using Pd(0) chemistry and cyclization of peptides, and for combinatorial strategies for producing large libraries of N-modified peptides.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of modifying a peptidic substrate attached to a solid support, wherein said peptidic substrate comprises a terminal primary alpha amine to generate a secondary amine the method comprising:

treating said peptidic substrate attached to a solid support with an aryl sulfonyl activating agent that, on reaction with said primary amine, results in an activated sulfonamide; and deprotonating said activated sulfonamide with a base having a pKa in the range of about 12 to 15 and selectively modifying the resulting deprotonated amide with a modifying agent to provide a substituted amide;

cleaving the activating group from said substituted amide to provide a substituted, secondary amine.

2. The method according to claim 1, wherein said peptidic substrate is a polypeptide comprising monomers selected from the group consisting of naturally occurring amino acids, amino acid analogs having modified side chains, peptide nucleic acids, and a combination thereof.

3. The method according to claim 1, wherein said aryl sulfonyl activating agent is an aryl sulfonyl halide substituted with an electron withdrawing group at the ortho or para position.

4. The method according to claim 3, wherein said aryl sulfonyl halide is ortho-nitrobenzenesulfonyl chloride or para-nitrobenzenesulfonyl chloride.

5. The method according to claim 1, wherein said base is a hindered guandidinium base.

6. The method according to claim 1, wherein said modifying agent is an electrophile.

7. The method according to claim 6, wherein said electrophile is an alkylating agent.

8. The method according to claim 1, wherein said cleaving step is an aromatic nucleophilic substitution effected with a thiol.

9. The method for introducing an N-alpha substituent at a specific site in a polypeptide during solid phase peptide synthesis, the method comprising:

synthesizing a polypeptide by stepwise addition of amino acids or analogs thereof while bound to a solid phase until the target residue has been added and deprotected to provide a free primary amine at an alpha position;

activating the alpha nitrogen by addition of an aryl sulfonyl activating agent that converts said primary amine to an activated sulfonamide;

deprotonating said activated sulfonamide with base having a pKa in the range from about 12 to 15 and selectively modifying the resulting deprotonated sulfonamide with a modifying agent to provide a substituted sulfonamide;

cleaving the aryl sulfonyl activating group from said substituted sulfonamide to provide a substituted, secondary amine; and continuing the stepwise addition of amino acids or analogs thereof to said polypeptide.

10. The method according to claim 9, wherein said aryl sulfonyl activating agent is an aryl sulfonyl halide substituted with an electron withdrawing group at the ortho or para position.

11. The method according to claim 10, wherein said aryl sulfonyl halide is ortho-nitrobenzenesulfonyl chloride or para-nitrobenzenesulfonyl chloride.

12. The method according to claim 9, wherein said base is a hindered guandidinium base.

13. The method according to claim 6, wherein said modifying agent is an electrophile.

14. The method according to claim 13, wherein said electrophile is an alkylating agent.

15. The method according to claim 9, wherein said cleaving step is an aromatic nucleophilic substitution effected with a thiol.

16. A method of synthesizing a library of compounds, the method comprising:

providing a library of peptidic substrates attached to a solid support, each of which comprises a terminal primary alpha amine group;

treating said library of peptidic substrates by addition of an ary sulfonyl activating agent that converts said primary amines to activated sulfonamides;

deprotonating said activated sulfonamides with base having a pKa in a range from about 12 to 15 and selectively modifying the resulting deprotonated sulfonamides with a modifying agent to provide substituted sulfonamides; and cleaving the aryl sulfonyl activating group from said substituted sulfonamides.

17. The method according to claim 16, wherein said library of target compounds comprises at least 1,000 different target compounds.

* * * * *